United States Patent [19]
Hardy, Jr. et al.

[11] 4,045,445
[45] Aug. 30, 1977

[54] 11-(4-PIPERIDYL)DIBENZO-DIAZEPINES

[75] Inventors: Robert Allis Hardy, Jr., Ridgewood, N.J.; Nicanor Quinones Quinones, New York, N.Y.

[73] Assignee: American Cyanamid Company, Stamford, Conn.

[21] Appl. No.: 637,564

[22] Filed: Dec. 14, 1975

[51] Int. Cl.$^2$ .......................................... C07D 401/04
[52] U.S. Cl. ...................... 260/293.59; 260/239 DD; 260/293.77; 260/293.79; 424/267
[58] Field of Search ................ 260/239 DD, 293.59

[56] References Cited

U.S. PATENT DOCUMENTS

| | | | |
|---|---|---|---|
| 3,532,702 | 10/1970 | Howell et al. | 260/293.4 |
| 3,539,573 | 11/1970 | Schmutz et al. | 260/268 |

*Primary Examiner*—Natalie Trousof
*Attorney, Agent, or Firm*—Denis A. Polyn

[57] ABSTRACT

The compounds, 11-(4-piperidyl)-5H-dibenzo[b,e][1,4]diazepines, intermediates and methods of preparation thereof are described. They are useful as neuroleptic agents.

20 Claims, No Drawings

11-(4-PIPERIDYL)DIBENZO-DIAZEPINES

BACKGROUND OF THE INVENTION

The novel compounds of this invention are related to the 11-(4-piperidyl)dibenz[b,f][1,4]oxazepines found in U.S. Pat. No. 3,501,483, and to the 11-basic substituted dibenzodiazepines found in U.S. Pat. No. 3,539,573, including clozapine [8-chloro-11-(4-methyl-1-piperazinyl)-5H-dibenzo[b,e]-[1,4]diazepine].

The standard neuroleptics, such as chlorpranazine [2-chloro-10-(3-dimethylaminopropyl)phenothiazine] and loxapine [2-chloro-11-(4-methyl-1-piperazinyl)-dibenz[b,f][1,4]-oxazepine] all show potent anti-apomorphine and cataleptogenic actions, and these actions are correlated with their extrapyramidal side effects [J. Schmutz, Arzneimittelforschung, 25, 712-720, (1975); Neuroleptic Piperazinyl-dibenzo-azepines].

Clozapine represents an effective anti-psychotic agent with a very low propensity for causing extrapyramidal reactions and, with clozapine, the absence of neuroleptic catalepsy and anti-apomorphine actions coincides with the absence of extrapyramidal side effects [D. DeMaio, Arzneimittelforschung, 22, (5), 919-923, (1972), Clozapine, a New Atypical Neuroleptic].

DESCRIPTION OF THE INVENTION

This invention relates to new organic compounds. More particularly it relates to 11-(4-piperidyl)-5H-dibenzo-[b,e][1,4]diazepines, intermediates, and methods of preparing the same.

The novel compounds of the present invention may be illustrated by the formula:

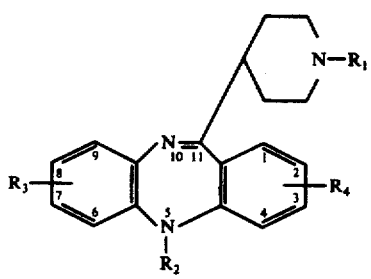

(I)

wherein $R_1$ is selected from the group consisting of hydrogen, $C_1$-$C_6$ alkyl, hydroxy $C_1$-$C_6$ alkyl, $C_1$-$C_{10}$ acyloxy $C_1$-$C_6$ alkyl, $C_1$-$C_6$ carboalkoxy, carbobenzoxy and benzyl; $R_2$ is selected from the group consisting of hydrogen and $C_1$-$C_6$ alkyl; $R_3$ and $R_4$ are selected from the group consisting of hydrogen, $C_1$-$C_6$ alkyl, $C_1$-$C_6$ alkoxy, $C_1$-$C_6$ alkyl mercapto, halogen, hydroxy, cyano, trifluoromethyl, nitro, di($C_1$-$C_6$ alkyl) sulfamoyl, $C_1$-$C_6$ alkanoyl, and may be mono substituted in either aromatic ring or disubstituted in both aromatic rings; and non-toxic acid addition salts thereof.

The compounds of the present invention possess valuable central nervous system (CNS) properties at non-toxic doses covering a wide range of therapeutic actions. As such, they show one or more of the following CNS actions: analgesics, neuroleptics, anxiolytics, antidepressants, sedatives, and antiemetics.

A further object of the present invention is to provide 8-substituted 11-(4-piperidyl)-5H-dibenzo[b,e][1,4]-diazepines as neuroleptic agents with a very low (or no) propensity for causing extrapyramidal reactions.

A preferred embodiment of the present invention is illustrated by the formula:

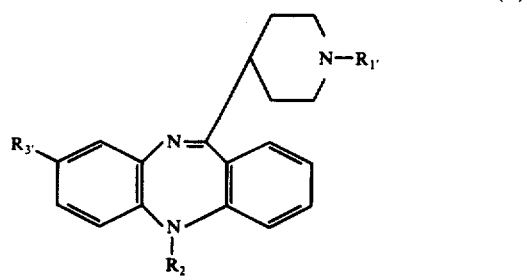

(II)

wherein $R_2$ is as hereinabove described; $R_{1'}$ is selected from the group consisting of hydrogen, $C_1$-$C_6$ alkyl and hydroxy $C_1$-$C_6$ alkyl; $R_{3'}$ is selected from the group consisting of hydrogen, halogen, $C_1$-$C_6$ alkyl, and trifluoromethyl; and non-toxic acid addition salts thereof.

Among those compounds contemplated by the present invention are the following:

8-Chloro-5-methyl-11-(1-methyl-4-piperidyl)-5H-dibenzo[b,e]-[1,4]diazepine

5-Methyl-11-(1-methyl-4-piperidyl)-5H-dibenzo[b,e][1,4]diazepine 5,8-Dimethyl-11-(1-methyl-4-piperidyl)-5H-dibenzo[b,e][1,4]-diazepine 5-Methyl-8-trifluoromethyl-11-(1-methyl-4-piperidyl)-5H-dibenzo[b,e][1,4]diazepine 8-Fluoro-5-methyl-11-(1-methyl-4-piperidyl)-5H-dibenzo[b,e]-[1,4]diazepine 8-Chloro-5-methyl-11-(4-piperidyl)-5H-dibenzo[b,e][1,4]diazepine 8-Chloro-5-methyl-11-[1-(2-hydroxyethyl)-4-piperidyl]-5H-dibenzo[b,e][1,4]diazepine 8-Chloro-11-(1-methyl-4-piperidyl)-5H-dibenzo[b,e][1,4]diazepine 8-Methyl-11-(1-methyl-4-piperidyl)-5H-dibenzo[b,e][1,4]diazepine 8-Trifluoromethyl-11-(1-methyl-4-piperidyl)-5H-dibenzo[b,e]-[1,4]diazepine 8-Fluoro-11-(1-methyl-4-piperidyl)-5H-dibenzo[b,e][1,4]diazepine 8-Chloro-2-hydroxy-11-(1-methyl-4-piperidyl)-5H-dibenzo-[b,e][1,4]diazepine 8-Chloro-3-hydroxy-11-(1-methyl-4-piperidyl)-5H-dibenzo-[b,e][1,4]diazepine 2-Chloro-11-(1-methyl-4-piperidyl)-5H-dibenzo[b,e][1,4]diazepine 2-Methyl-11-(1-methyl-4-piperidyl)-5H-dibenzo[b,e][1,4]diazepine 2-Methoxy-11-(1-methyl-4-piperidyl)-5H-dibenzo[b,e][1,4]diazepine 2-Methylthio-11-(1-methyl-4-piperidyl)-5H-dibenzo[b,e][1,4]-diazepine 8-Dimethylsulfamoyl-5-methyl-11-(1-methyl-4-piperidyl)-5H-dibenzo[b,e][1,4]diazepine 5-Methyl-2-nitro-11-(1-methyl-4-piperidyl)-5H-dibenzo[b,e]-[1,4]diazepine 8-Acetyl-5-methyl-11-(1-methyl-4-piperidyl)-5H-dibenzo[b,e]-[1,4]diazepine 8-Chloro-11-(4-piperidyl)-5H-dibenzo[b,e][1,4]diazepine 8-Chloro-11-(1-ethyl-4-piperidyl)-5H-dibenzo[b,e][1,4]diazepine 8-Chloro-5-ethyl-11-(1-methyl-4-piperidyl)-5H-dibenzo[b,e]-[1,4]diazepine 11-(1-Methyl-4-piperidyl)-5H-dibenzo[b,e][1,4]diazepine 7-Chloro-5-methyl-11-(1-methyl-4-piperidyl)-5H-dibenzo[b,e]-[1,4]diazepine 2-Chloro-5-methyl-11-(1-methyl-4-piperidyl)-5H-dibenzo[b,e]-[1,4]diazepine 8-Chloro-11-(1-carbethoxy-4-piperidyl)-5H-dibenzo[b,e][1,4]-diazepine 2-Chloro-11-(1-carbobenzoxy-4-piperidyl)-5H-dibenzo[b,e]-[1,4]diazepine 2-Chloro-11-(1-benzyl-4-piperidyl)-5H-dibenzo[b,e][1,4]diazepine 5-Methyl-2-nitro-11-(1-methyl-4-piperidyl)-5H-dibenzo[b,e]-[1,4]diazepine 5-Methyl-2-methylthio-11-(1-methyl-4-piperidyl)-5H-dibenzo[b,e][1,4]diazepine 8-Cyano-5-methyl-11-(1-methyl-4-piperidyl)-5H-dibenzo[b,e]-[1,4]diazepine Certain of the above 8-substituted 5H-dibenzo[b,e][1,4]diazepines provide an improved therapeutic treatment comprising a novel neuroleptic action with little or no propensity to cause extrapyramidal side effects.

The novel activity pattern of the 8-substituted-5H-dibenzo[b,e][1,4]diazepines of the present invention is displayed by their actions in a group of pharmacological and biochemical procedures taken as a whole rather than by the results of any individual test. Initial classification of the novel neuroleptic profile of the 8-substituted-5H-dibenzo[b,e][1,4]diazepines of the present invention is provided by the following procedures: (1) Inhibition of motor activity in rats; (2) Inhibition of motor actvity in mice; (3) Lack of antagonism of apomorphine-induced gnawing at therapeutic levels; (4) Lack of neuroleptic catalepsy at therapeutic doses. The profile of actions of the 8-substituted-5H-dibenzo[b,e][1,4]-diazepines of the present invention represent a novel activity pattern as a new class of neuroleptic agent. As such they differ markedly from the classical neuroleptic agents in their pharmalogical and biochemical profile, indicating a very low propensity for causing extrapyramidal reactions. This represents a unique and very desirable property for a psychotropic drug used in the treatment of psychotropic disorders, since many, if not most, of the established neuroleptic drugs produce undesirable extrapyramidal symptoms when used at therapeutic levels over a period of time. This usually requires concomitant treatment with anticholinergic drugs to alleviate the extrapyramidal side effects while maintaining the therapeutic benefit of the neuroleptic drug.

A further preferred embodiment of the present invention is illustrated by the formula:

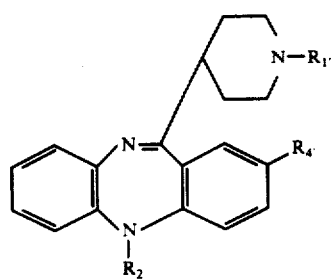

(III)

wherein $R_1$ and $R_2$ are as described hereinbefore; $R_4$ is selected from the group consisting of halogen, $C_1$–$C_6$ alkyl, $C_1$–$C_6$ alkoxy, trifluoromethyl; and non-toxic acid addition salts thereof. The activity pattern of the above described 2-substituted 5H-dibenzo[b,e][1,4]diazepines of this invention is displayed by one or more of the following CNS actions: analgesics, neuroleptics, anxiolytics, antidepressants, sedatives and antiemetics. These actions are evident in animal experimentation using procedures well known to those skilled in the art.

For example, to determine analgesic activity a modification of the method of Randall and Selitto [Arch. Int. Pharmacodyn., 111, 409 (1957)] may be used. This test measures the pain threshold of rats whose paws are made sensitive to pressure by the injection of 0.1 ml of a 20% aqueous suspension of brewers' yeast into the plantar surface of the left hind paw. Constantly increasing force (16g/second) is applied to the swollen paw using an Analgesey Meter, Ugo Basile. The pressure is cut off at 250 g of force if there is no response (sudden stuggle or vocalization). Control rats treated with starch vehicle respond to a pressure of about 30 g. Pressure-pain thresholds are always recorded 2 hours after administration of brewers' yeast. Test compounds are administered at the same time as the yeast at an appropriate oral dose. Ratios of treated (T)/control (C) reaction thresholds are calculated as estimates of analgesic efficacy (degree of analgesia obtainable). Test compounds are considered active if they produce a 100% elevation of pain threshold (T/C $\geq$ 1.37).

To determine anti-anxiety activity the compounds may be tested to show their ability to protect warm-blooded animals from convulsions resulting from administration of pentylenetetrazol. Graded dose levels of the test compounds are administered orally in a 2% starch vehicle to groups of at least 5 rats. At the estimated time of peak effect, the rats are treated intravenously with pentylenetetrazol at a dose of 21 to 23 mg/Kg of body weight. This dose is estimated to cause clonic seizures in 99% of unprotected rats. The effective dose of the test compounds which provides protection for 50% of the animals is calculated by the method of D. H. Finney in Statistical Methods in Biological Assay, Second Edition, Hofner Publishing Co., New York, 456–457, (1964), or by the method of J. T. Litchfield and J. Wilcoxon, Pharmacol. and Exp. Ther., 96, 99 (1949).

The anti-depressant properties of the compounds of the present invention may be determined by measuring their ability to counteract a depression induced in animals by the administration of tetrabenazine hexamate. Graded doses of the test compounds are administered to groups of 5 mice each and this is followed by administering a dose of tetrabenazine hexamate which is known to markedly depress the exploratory behavior of normal mice. The anti-depressant treated groups show normal exploratory behavior, while the control groups, and groups treated with an ineffective anti-depressant agent, do not show normal exploratory behavior, but show the well known, profound depression induced by tetrabenazine.

The new compounds of this invention are, in general, oils or solids only slightly soluble in water, but soluble in organic solvents such as methanol, ethanol and the like. They are basic substances which are usually soluble in aqueous mineral acids and in solution of organic acids such as acetic acid. They form acid addition salts, such as the hydrochloride, sulfate, phosphate, citrate, tartrate, maleate, fumarate, etc. The bases as well as their acid addition salts can be used as active substances in pharmaceuticals. As such they may be administered orally or parenterally and when so administered produce a therapeutically desired effect for the treatment of a variety of CNS conditions including psychotic disorders such as acute and chronic schizophrenia.

A wide range of doses may be employed. Individual doses may range from about 25 to about 400 mg, and a preferred range is from about 50 to about 250 mg. The dosage range is adjusted to provide an optimum therapeutic response in the warm-blooded animal being treated. Thus, for example, several doses may be administered daily, or the dose may be reduced proportionately as indicated by the exigencies of the therapeutic situation. The daily dosage range is from about one to about 20 mg/Kg with a preferred range of about 4 to about 10 mg/Kg.

For therapeutic administration an active dibenzodiazepine, or salt, of this invention may be incorporated with excipients and used, for example, in the form of tablets, dragees, capsules, suppositories, liquids, elixirs, emulsions, suspensions, syrups, chocolate, candy, wafers, chewing gum, solutions for parenteral administration, or the like. Such compositions and preparations should contain at least 0.1% of active dibenzodiazepine or salt. The percentage in the compositions and preparations may, of course, be varied, and may conveniently be between about 2% and 60% or more of the weight of the unit. The amount of active dibenzodiazepine, or salt, in such therapeutically useful antipsychotic compositions or preparations is such that a suitable dosage will be obtained. This dosage can also be obtained by the use of sustained release preparations. Preferred compositions or preparations according to the present invention are prepared so that a dosage unit form contains between about 25 and about 400 mg of the active dibenzodiazepine or salt.

Tablets, pills, dragees, and the like may contain the following: a binder such as gum tragacanth, acacia, corn starch, or gelatin. A disintegrating agent such as corn starch, potato starch, alginic acid, or the like. A lubricant such as stearic acid, magnesium stearate, talc, or the like. A sweetening agent such as sucaryl or saccharin may be added, as well as a flavoring such as peppermint, oil of wintergreen or cherry flavoring.

The novel compounds of this invention may be prepared by a number of methods which are described hereinafter. By a preferred method, a suitably substituted 2'-arylamino-isonipecotanilide (IV) is cyclized to yield the desired 11-(4-piperidyl)-5H-dibenzo[b,e][1,4]-diazepine (I). This method is illustrated as follows:

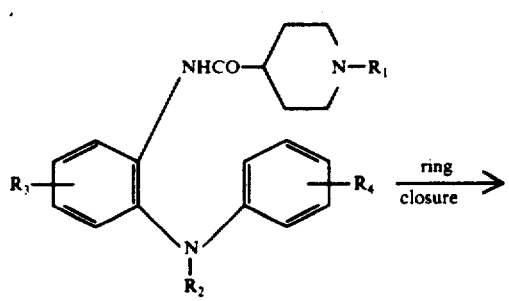

(IV)

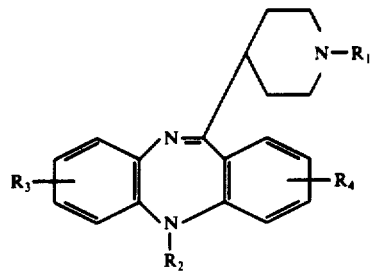

wherein $R_1$, $R_2$, $R_3$ and $R_4$ are as previously described. By this method the appropriately substituted isonipecotanilides are subjected to intramolecular cyclodehydration (Bishler-Napieralski ring closure) in the presence of a dehydrating agent such as phosphorus oxychloride, phosphorus pentoxide, phosphorus pentachloride, polyphosphoric acid, zinc chloride, aluminum chloride, thionyl chloride, and the like either alone or in combination, preferably in the presence of an inert solvent such as benzene, xylene, o-dichlorobenzene and the like. This reaction is generally carried out at an elevated temperature but the temperature may range from about 50° C to about 240° C. The reaction is usually complete within about 8 to 20 hours but may take as long as 2 to 4 days with mild reagents at low temperatures. The required substituted isonipecotanilides (IV) are readily prepared by acylation of known o-aminodiphenylamines with the desired substituted isonipecotic acid halide hydrohalide. This reaction is generally effected in an inert solvent such as acetone, benzene, dimethylformamide and the like in the presence of an alkaline reagent such as triethylamine, pyridine, dimethylaniline, and the like.

In order to obtain products of Formula I wherein $R_2$ is hydrogen and using the above cyclization procedure, a protecting group ($R_2'$) is employed and is split off in a known manner after ring closure. Suitable protecting groups which can be split off by standard procedures, such as selective hydrolysis or hydrogenolysis are 5-acetyl, 5-benzoyl, 5-benzyl and 5-carbobenzoxy.

Another preferred method is represented by the cyclization of a substituted 2-(o-aminophenylamino)phenyl 4-piperidyl ketone (V) as follows:

(V)

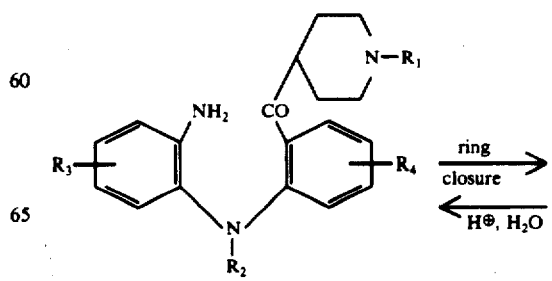

(I)

-continued

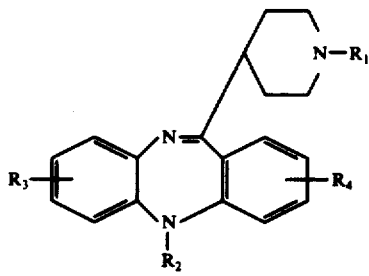

wherein $R_1$, $R_2$, $R_3$ and $R_4$ are as previously described. This cyclization may be carried out in a solvent such as acetone, benzene, water or alcohol in the presence of an acidic catalyst, or in the presence of a dehydrating agent with or without an inert solvent. Suitable acidic catalysts are hydrochloric acid, sulfuric acid, p-toluenesulfonic acid, fumaric acid and the like. Suitable dehydrating agents are zinc chloride, phosphorus pentachloride, phosphorus oxychloride, phosphorus pentoxide and the like. The temperature is not critical and may range from about 20° C to about 150° C. Cyclization may be effected by virtue of the equilibrium mixtures of I and V formed in dilute aqueous acids. The ketones (V) and the dibenzo[b,e][1,4]diazepines (I) are readily interconverted under acidic conditions or in the presence of an acidic catalyst. Isolation of either one or both components from mixtures containing I and V is dependent upon the individual properties of the equilibrium pair. Physical properties such as differential solubilities of the bases and/or acid addition salts may thus determine which of these components is more readily isolated from a given mixture. The proportions of each component will also vary in the equilibrium mixtures; which also influences the ease of isolation of the desired compound. Standard methods of separation and purification well known to those skilled in the art are used for isolation of the desired products; these include extraction, fractional crystallization, chromatographic separation and purification, and the like. In general, the corresponding individual ketone products (V) and the 5H-dibenzo[b,e][1,4]diazepines (I) of this invention both show similar CNS actions.

As shown in the above equilibrium scheme, the substituted 2-(o-aminophenylamino)phenyl 4-piperidyl ketones (V) may be obtained with the corresponding 11-(4-piperidyl)-5H-dibenzo[b,e][1,4]diazepines (I), or in some instances may be the sole product isolated, when a suitably substituted 2'-phenylamio-isonipecotanilide (IV) is cyclized to the corresponding dibenzo-diazepine (I). Recyclization of the amino ketone (V) to the dibenzo-diazepine (I) may then be effected under the above described conditions. Cleavage of the dibenzo-diazepines (I) back to the 2'-phenylamino-isonipecotanilide starting materials (IV) does not take place.

Another method applicable to the preparation of the new compounds of this invention is illustrated as follows:

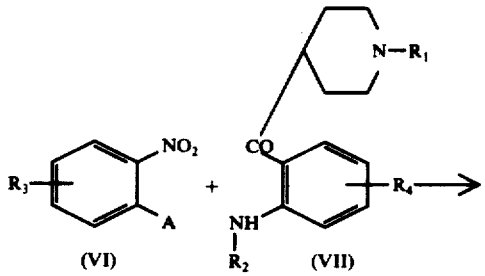

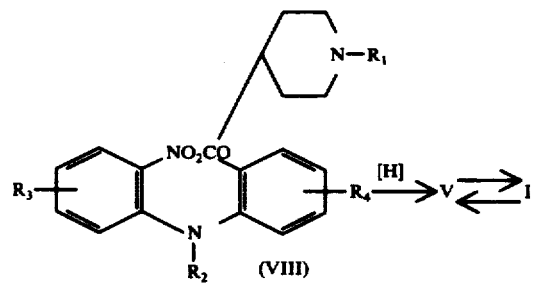

wherein $R_1$, $R_2$, $R_3$ and $R_4$ are as hereinbefore described, and A represents a halogen atom of atomic weight less than 80. By this procedure an o-halonitrobenzene (VI) is reacted with an o-aminophenyl 4-piperidyl ketone (VII) in an Ullman-type reaction to give the 2-(o-nitrophenylamino)phenyl ketone derivative (VIII). Reduction of the o-nitro group then gives the amino ketones (V) which are cyclized to the dibenzodiazepines (I) as described above. The o-aminophenyl 4-piperidyl ketones are synthesized by standard methods known to those skilled in the art. For example, a ketone synthesis using a 1-substituted-4-piperidyl organometallic reagent such as the magnesium bromide or the lithio derivative may be employed. Treatment of this organo-metal reagent with an o-nitrobenzoyl halide, with a 2-methyl-4H-3,1-benzoxazin-4-one, or with an isatin then produces an o-nitrophenyl, o-acetamidophenyl or o-aminophenyl 1-methyl-4-piperidyl ketone. The o-nitro or o-acetamido derivatives are then converted to the desired o-aminophenyl ketones (VII) by reduction or hydrolysis. General methods for o-aminophenyl ketones have been reviewed by J. C. E. Simpson, et al, J. Chem. Soc. (1945), p. 646 and by L. H. Sternback, et al, J. Org. Chem. 27, 3781 (1962). Another method for the o-aminophenyl ketone intermediates (VII) comprieses Friedel Crafts acylation of a para-substituted aniline (such as p-chloroacetanilide) with an isonipecotoyl chloride followed by hydrolysis. Hydrogenolysis of the para-chloro (or other halo)-o-acylacetanilide derivatives followed by hydrolysis also gives o-aminophenyl 1-substituted-4-piperidyl ketones without additional substituents in the o-aminophenyl ring. These procedures are similar to the methods described by R. E. Lyle, et al, J. Org. Chem. 24, 338 (1959), and by L. H. Sternbach, et al, J. Org. Chem. 27, 3781 (1962).

Another synthesis of the new 11-(4-piperidyl)-5H-dibenzo[b,e][1,4]diazepines of this invention comprises side chain cyclization on a substituted dibenzodiazepine as follows:

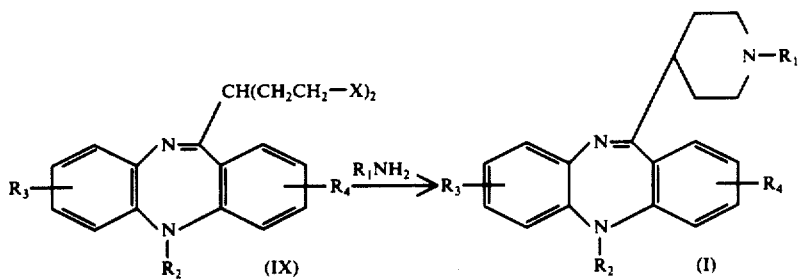

wherein $R_1$, $R_2$, $R_3$ and $R_4$ are as hereinbefore described, and X is a suitably reactive group such as halogen or arylsulfonyloxy (such as tosyloxy) and the like.

Additionally, other substituents which are transformable, by methods known to those skilled in the art, into $R_1$, $R_2$, $R_3$ and $R_4$ of Formula I may also provide methods for preparation of the new compounds of this invention. Illustrative of such sequences are the conversion of carbethoxy or carbobenzoxy to hydrogen for $R_1 = H$ or $R_2 = H$ by selective hydrolysis, and conversion of $R_1 = H$ and/or $R_2 = H$ to a $C_1-C_6$ alkyl residue such as methyl by alkylation with an alkyl halide, sulfate or arylsulfonate generally in the presence of a basic catalyst. Also, a variety of substituents on the aromatic rings such as amino, nitro, diazonium, and halogen groups may be converted to the $R_3$ and $R_4$ groups either directly or sequentially by well known methods.

SPECIFIC DISCLOSURE

The following examples illustrate in detail the preparation of representative 11-(4-piperidyl)-5H-dibenzo[b,e][1,4]diazepines of this invention and their intermediates.

EXAMPLE 1

8-Chloro-5-methyl-11-(1-methyl-4-piperidyl)-5H-dibenzo[b,e]-[1,4]diazepine

4-Chloro-2-nitro-N-methyldiphenylamine, [mp 71° – 72° C (Storrie and Tucker, J. Chem. Soc. (1931), 2255)] is reduced with zinc and ammonium chloride in ethanol solution and 2-amino-4-chloro-N-methyldiphenylamine is thereby obtained.

To a mixture of 10 g (0.05 mole) of 2-amino-4-chloro-N-methyldiphenylamine and 10 ml of pyridine in 100 ml of benzene is added slowly, with stirring at room temperature, 10 g (0.05mole) of 1-methylisonipecotoyl chloride hydrochloride. After the addition is complete the mixture is heated on a steam bath under reflux for about 3 hours. The reaction mixture is evaporated under reduced pressure to a solid residue and 200 ml of water and 200 ml of concentrated ammonium hydroxide are added. An oily precipitate is obtained and is extracted into 100 ml of ether. The ether layer is dried over anhydrous potassium carbonate, and then evaporated to a viscous oil. This crude product is dissolved in ether, extracted into dilute acetic acid solution, and the aqueous acidic layer is made basic with concentrated ammonium hydroxide. The reprecipitated product is reextracted into ether. The ether layer is dried and evaporated to an oily residue which is taken up in 400 ml of petroleum ether. The mixture is filtered and evaporated again to give 6 g of 5'-chloro-1-methyl-2'-(N-methylanilino)isonipecotanilide as a non-crystalline base. The hydrochloride has a m.p. 260°–263° C (dec.), prepared by treating an ether solution of the base with alcoholic hydrogen chloride.

A mixture of 6.0 g of 5'-chloro-1-methyl-2'-(N-methylanilino)isonipectanilide base and 7 g of phosphorus pentoxide in 25 ml of phosphorous oxychloride is heated to reflux overnight. After about 20 hours the cooled reaction mixture is poured onto ice with vigorous mixing and cooling (0°–10° C); a total volume of about 500 ml of acidic solution is produced. The acidic solution is filtered into concentrated ammonium hydroxide with stirring, and a light yellow solid is formed. The precipitate is collected, dissolved in 100 ml of ether, and the mixture is filtered to remove a dark brown gum, and evaporated to a solid which is recrystallized from petroleum ether by evaporation to give 2.6 g (46% of theory) of product, mp 142°–146° C. This material is dissolved in 50 ml of boiling hexane, filtered to remove a trace of insoluble precipitate, and the filtrate is clarified with activated charcoal and diatomaceous earth and evaporated to about 30 ml. After crystallization at 0° C, the product, 1.5 g of 8-chloro-5-methyl-11-(1-methyl-4-piperidyl)-5H-dibenzo[b,e][1,4]diazepine, mp 143°–145° C, is collected and dried under reduced pressure.

This compound shows an activity profile as a neuroleptic agent with a low propensity for extrapyramidal side effects. It reduces motor activity, is active in enhancing apomorphine-induced biting and gnawing at 8 mg/Kg, and does not antagonize apomorphine-induced gnawing and biting at therapeutic doses. It is also active as an analgesic.

EXAMPLE 2

5-Methyl-11-(1-methyl-4-piperidyl)-5H-dibenzo[b,e][1,4]diazepine

The general procedures of Example 1 are repeated: From 39 g of 2-amino-N-methyldiphenylamine and 39 g of 1-methylisonipecotoyl chloride hydrochloride, crude 1-methyl-2'-(N-methylanilino)isonipecotanilide is obtained as an oil and purified by distillation. The fumarate salt, prepared in acetone solution, melts at 129° C.

A mixture of 9 g of crude 1-methyl-2'-(N-methylanilino)isonipecotanilide base, 10 g of phosphorus pentoxide and 30 ml of phosphorus oxychloride is heated under reflux for 4 hours, and the reaction mixture is diluted with ether and slowly added to an ice-cold solution of ammonium hydroxide. The mixture is filtered, and the ether layer is separated, dried over anhydrous potassium carbonate and evaporated to yellow solid residue (8.0 g). This crude cyclized base is dissolved in 100 ml of dilute acetic acid, the solution is clarified with activated charcoal and the filtrate is made basic with ammonium hydroxide. The precipitated base is collected, dissolved in 30 ml of ether, and the ether layer is dried over anhydrous potassium carbonate. This solution is filtered into 100 ml of petroleum ether. The product crystallizes as a yellow solid and is collected and dried in vacuo; 5-methyl-11-(1-methyl-4-piperidyl)-5H-dibenzo[b,e][1,4]-diazepine, m.p. 119°-121° C., is thereby obtained; IR (KBr) 6.15 μ (anil C=N).

EXAMPLE 3

2-Chloro-5-methyl-11-(1-methyl-4-piperidyl)-5H-dibenzo[b,e]-[1,4]diazepine

The general procedures of Example 1 are repeated: From 2-amino-4'-chloro-N-methyldiphenylamine and 1-methylisonipecotoyl chloride hydrochloride, 2'-(p-chloro-N-methylanilino)-1-methylisonipecotanilide is obtained.

A mixture of crude 2'-(p-chloro-N-methylanilino-1-methylisonipecotanilide with phosphorus pentoxide and phosphorus oxychloride is heated under reflux, and the reaction mixture is worked up as described in Example 1. 2-Chloro-5-methyl-11-(1-methyl-4-piperidyl)-5H-dibenzo[b,e][1,4]diazepine is thereby obtained.

EXAMPLE 4

2-Chloro-5-methyl-11-(4-piperidyl)-5H-dibenzo[b,e][1,4]diazepine

The compound 2'-(p-chloro-N-methylanilino)isonipecotanilide, prepared by hydrolysis of the corresponding 1-carbobenzoxyisonipecotanilide, is cyclized by the procedure of Example 1 and, after isolation and purification of the product, 2-chloro-5-methyl-11-(4-piperidyl)-5H-dibenzo[b,e][1,4]-diazepine is thereby obtained.

EXAMPLE 5

2-Chloro-5-methyl-11-[1-(2-hydroxyethyl)-4-piperidyl]-5H-dibenzo[b,e][1,4]diazepine The compound 2-chloro-5-methyl-11-(4-piperidyl)-5H-dibenzo[b,e][1,4]diazepine (Example 3) is reacted with 2-bromoethanol in benzene solution in the presence of pyridine, and 2-Chloro-5-methyl-11-[1-(2-hydroxyethyl)-4-piperidyl]-5H-dibenzo[b,e][1,4]diazepine is thereby obtained.

EXAMPLE 6

8-Chloro-11-(1-methyl-4-piperidyl)-5H-dibenzo[b,e][1,4]diazepine

A mixture of o-(2-amino-4-chloroanilino)phenyl 1-methyl-4-piperidyl ketone and phosphorus oxychloride is warmed on the steam bath. The reaction mixture is concentrated in vacuo to remove excess phosphorus oxychloride, benzene is added and the process is repeated. The residue is then distributed between benzene and ammonium hydroxide/ice water. Separation of the benzene layer and purification of the basic component is carried out as described in Example 2. The crude cyclized base is dissolved in dilute acetic acid solution, the mixture is clarified with activated charcoal and diatomaceous earth and the filtrate is made basic with ammonium hydroxide. The precipitated base is collected, dissolved in ether, and the ether layer is dried over anhydrous potassium carbonate. Evaporation of the ether then gives 8-chloro-11-(1-methyl-4-piperidyl)-5H-dibenzo[b,e][1,4]diazepine base.

The o-(2-amino-4-chloroanilino)phenyl 1-methyl-4-piperidyl ketone used as the starting material can be obtained by reduction of o-(4-chloro-2-nitroanilino)-phenyl 1-methyl-4-piperidyl ketone which, in turn, is prepared from o-aminophenyl 1-methyl-4-piperidyl ketone and 1,4-dichloro-2-nitrobenzene. Reduction of o-(4-chloro-2-nitroanilino)phenyl 1-methyl-4-piperidyl ketone and cyclization to the desired 8-chloro-11-(1-methyl-4-piperidyl)-5H-dibenzo[b,e][1,4]diazepine may also be carried out without isolation and purification of the above described o-(2-aminoanilino)phenyl ketone intermediate.

The required o-aminophenyl 1-methyl-4-piperidyl ketone may, in turn, be prepared as follows: Friedel Crafts acylation of p-chloroacetanilide with 1-methylisonipecotoyl chloride gives 2-acetamido-5-chlorophenyl 1-methyl-4-piperidyl ketone, this intermediate is hydrogenated in the presence of a catalyst (to remove the p-chloro moiety) followed by hydrolysis of the N-acetyl group, and o-aminophenyl 1-methyl-4-piperidyl ketone is obtained.

EXAMPLE 7

8-Methyl-11-(1-methyl-4-piperidyl)-5H-dibenzo[b,e][1,4]diazepine

The general procedures of Example 6 are repeated. The compound o-(2-nitro-p-toluidino)phenyl 1-methyl-4-piperidyl ketone is reduced and cyclized to give 8-methyl-11-(1-methyl-4-piperidyl)-5H-dibenzo[b,e][1,4]-diazepine.

EXAMPLE 8

8-Trifluoromethyl-11-(1-methyl-4-piperidyl)-5H-dibenzo[b,e]- [1,4]diazepine

The general procedures of Example 6 are repeated whereby o-(2-nitro-α,α,α-trifluoro-p-toluidino)phenyl 1-methyl-4-piperidyl ketone is reduced and cyclized. 8-Trifluoromethyl-11-(1-methyl-4-piperidyl)-5H-dibenzo[b,e][1,4]diazepine is thereby obtained.

EXAMPLE 9

8-Fluoro-11-(1-methyl-4-piperidyl)-5H-dibenzo[b,e][1,4]diazepine

The general procedures of Example 6 are repeated. The compound o-(4-fluoro-2-nitroanilino)phenyl 1-methyl-4-piperidyl ketone is reduced and cyclized with phosphorus oxychloride to give 8-fluoro-11-(1-methyl-4-piperidyl)-5H-dibenzo[b,e][1,4]diazepine base, which is converted to the fumarate salt.

EXAMPLE 10

2-Chloro-11-(1-methyl-4-piperidyl)-5H-dibenzo[b,e][1,4]diazepine

The general procedures of Example 6 are repeated: 2-amino-5-chlorophenyl 1-methyl-4-piperidyl ketone is prepared by previously described procedures, and is reacted with o-chloronitrobenzene to give 5-chloro-2-(o-nitroanilino)phenyl 1-methyl-4-piperidyl ketone. This intermediate is reduced with zinc and ammonium chloride and cyclized in the presence of an acidic catalyst to give 2-chloro-11-(1-methyl-4-piperidyl)-5H-dibenzo[b,e][1,4]diazepine.

EXAMPLE 11

2-Methyl-11-(1-methyl-4-piperidyl)-5H-dibenzo[b,e][1,4]diazepine

In a manner similar to the methods of Examples 6 and 10, 6-(o-nitroanilino)-m-tolyl 1-methyl-4-piperidyl ketone is prepared and reduced to the corresponding o- aminoanilino derivative which is cyclized in the presence of an acidic catalyst to give 2-methyl-11-(1-methyl-4-piperidyl)-5H-dibenzo[b,e][1,4]diazepine.

EXAMPLE 12

2-Fluoro-11-(1-methyl-4-piperidyl)-5H-dibenzo[b,e][1,4]diazepine

By analogous procedures as in Examples 6 and 10, using the corresponding starting materials, 2-amino-5-fluorophenyl 1-methyl-4-piperidyl ketone is prepared and reacted with o-chloronitrobenzene to give 5-fluoro-2-(o-nitroanilino)-phenyl 1-methyl-4-piperidyl ketone. This intermediate is then reduced and cyclized in the presence of an acidic catalyst to give 2-fluoro-11-(1-methyl-4-piperidyl)-5H-dibenzo-[b,e][1,4]diazepine.

EXAMPLE 13

8-Chloro-11-(1-ethyl-4-piperidyl)-5-methyl-5H-dibenzo[b,e]-[1,4]diazepine

The general procedures of Example 1 are repeated. From 2-amino-4-chloro-N-methyldiphenylamine and 1-ethylisonipecotoyl chloride, 5'-chloro-1-ethyl-2'-(N-methylanilino)-isonipecotanilide is prepared. This intermediate is cyclized by heating with a mixture of phosphorus oxychloride and phosphorus pentoxide and, after isolation and purification by the methods described in Examples 1 and 2, 8-chloro-11-(1-ethyl-4-piperidyl)-5-methyl-5H-dibenzo[b,e][1,4]diazepine is obtained.

EXAMPLE 14

8-Chloro-5-ethyl-11-(1-methyl-4-piperidyl)-5H-dibenzo[b,e]-[1,4]diazepine

The general procedures of Example 1 are repeated. The compound 4-chloro-N-ethyl-2-nitrodiphenylamine is prepared, is reduced and converted to 5'-chloro-1-methyl-2'-(N-ethylanilino)isonipecotanilide base. This isonipecotanilide is cyclized with phosphorus pentoxide and phosphorus oxychloride and, after isolation and purification, 8-chloro-5-ethyl-11-(1-methyl-4-piperidyl)-5H-dibenzo[b,e][1,4]diazepine is thereby obtained.

EXAMPLE 15

8-Methoxy-5-methyl-1-(1-methyl-4-piperidyl)-5H-dibenzo[b,e]-[1,4]diazepine

The general procedures of Examples 1 and 2 are repeated. The compound 4-methoxy-N-methyl-2-nitrodiphenylamine is prepared and reduced to the corresponding 2-amino derivative which is converted to 5'-methoxy-1-methyl-2'-(N-methylanilino)isonipecotanilide. This isonipecotanilide base is treated with phosphorus pentoxide/phosphorus oxychloride, the cyclized product is isolated and purified and 8-methoxy-5-methyl-11-(1-methyl-4-piperidyl)-5H-dibenzo[b,e]-[1,4]diazepine is obtained.

EXAMPLE 16

2-Chloro-7-methoxy-5-methyl-11-(1-methyl-4-piperidyl)-5H-dibenzo[b,e][1,4]diazepine By procedures analogous to the methods of Examples 1 and 2, 4'-chloro-5-methoxy-N-methyl-2-nitrodiphenylamine is prepared and converted to 2'-(p-chloro-N-methylanilino)-4'-methoxy-1-methylisonipecotanilide by reduction followed by amide formation. The preceding isonipecotanilide is cyclized with phosphorus oxychloride and phosphorus pentoxide and 2-chloro-7-methoxy-5-methyl-11-(1-methyl-4-piperidyl)-5H-dibenzo[b,e][1,4]diazepine is thereby obtained.

EXAMPLE 17

2-Chloro-7-hydroxy-5-methyl-11-(1-methyl-4-piperidyl)-5H-dibenzo[b,e][1,4]diazepine The compound 2-chloro-7-methoxy-5-methyl-11-(1-methyl-4-piperidyl)-5H-dibenzo[b,e][1,4]diazepine is heated with pyridine hydrochloride and 2-chloro-7-hydroxy-5-methyl-11-(1-methyl-4-piperidyl)-5H-dibenzo[b,e][1,4]diazepine is thereby obtained.

We claim:

1. A compound of the formula:

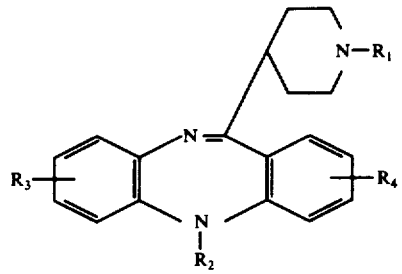

wherein $R_1$ is selected from the group consisting of hydrogen, $C_1$–$C_3$ alkyl, and hydroxy $C_1$–$C_3$ alkyl; $R_2$ is selected from the group consisting of hydrogen and $C_1$–$C_3$ alkyl; $R_3$ and $R_4$ are selected from the group consisting of hydrogen, $C_1$–$C_3$ alkyl, $C_1$–$C_3$ alkoxy, halogen, hydroxy and trifluoromethyl; and nontoxic acid addition salts thereof.

2. A compound according to claim 1, wherein $R_1$ is selected from the group consisting of hydrogen, $C_1$–$C_3$ alkyl and hydroxy ethyl; $R_2$ is selected from the group consisting of hydrogen and $C_1$–$C_3$ alkyl; $R_3$ is at the carbon eight position and is selected from the group consisting of hydrogen, halogen, $C_1$–$C_3$ alkyl, $C_1$–$C_3$ alkoxy, and trifluoromethyl; $R_4$ is hydrogen; and non-toxic acid addition salts thereof.

3. A compound according to claim 1, wherein $R_1$ is selectee from the group consisting of hydrogen, $C_1$–$C_3$ alkyl and hydroxy ethyl; $R_2$ is selected from the group consisting of hydrogen and $C_1$–$C_3$ alkyl; $R_3$ is hydrogen; $R_4$ is at the carbon two position and is selected from the group consisting of halogen, $C_1$–$C_3$ alkyl, trifluoromethyl, and $C_1$–$C_3$ alkoxy; and non-toxic acid addition salts thereof.

4. The compound according to claim 1, 8-Chloro-5-methyl-11-(1-methyl-4-piperidyl)-5H-dibenzo[b,e][1,4]-diazepine.

5. The compound according to claim 1, 5-Methyl-11-(1-methyl-4-piperidyl)-5H-dibenzo[b,e][1,4]diazepine.

6. The compound according to claim 1, 8-Methoxy-5-methyl-11-(1-methyl-4-piperidyl)-5H-dibenzo[b,e][1,4]-diazepine.

7. The compound according to claim 1, 8-Chloro-11-(1-methyl-4-piperidyl)-5H-dibenzo[b,e][1,4]diazepine.

8. The compound according to claim 1, 8-Methyl-11-(1-methyl-4-piperidyl)-5H-dibenzo[b,e][1,4]diazepine.

9. The compound according to claim 1, 8-Trifluoromethyl-11-(1-methyl-4-piperidyl)-5H-dibenzo[b,e][1,4]diazepine.

10. The compound according to claim 1, 8-Fluoro-11-(1-methyl-4-piperidyl)-5H-dibenzo[b,e][1,4]diazepine.

11. The compound according to claim 1, 2-Fluoro-11-(1-methyl-4-piperidyl)-5H-dibenzo[b,e][1,4]diazepine.

12. The compound according to claim 1, 2-Chloro-11-(1-methyl-4-piperidyl)-5H-dibenzo[b,e][1,4]diazepine.

13. The compound according to claim 1, 2-Methyl-11-(1-methyl-4-piperidyl)-5H-dibenzo[b,e][1,4]diazepine.

14. The compound according to claim 1, 2-Chloro-5-methyl-11-(4-piperidyl)-5H-dibenzo[b,e][1,4]diazepine.

15. The compound according to claim 1, 8-Chloro-11-(1-ethyl-4-piperidyl)-5-methyl-5H-dibenzo[b,e][1,4]-diazepine.

16. The compound according to claim 1, 8-Chloro-5-ethyl-11-(1-methyl-4-piperidyl)-5H-dibenzo[b,e][1,4]-diazepine.

17. The compound according to claim 1, 2-Chloro-5-methyl-11-(1-methyl-4-piperidyl)-5H-dibenzo[b,e][1,4]-diazepine.

18. The compound according to claim 1, 2-Chloro-5-methyl-11-[1-(2-hydroxyethyl)-4-piperidyl]-5H-dibenzo[b,f]-[1,4]diazepine.

19. The compound according to claim 1, 2-Chloro-7-methoxy-5-methyl-11-(1-methyl-4-piperidyl)-5H-dibenzo[b,f]-[1,4]diazepine.

20. The compound according to claim 1, 2-Chloro-7-hydroxy-5-methyl-11-(1-methyl-4-piperidyl)-5H-dibenzo[b,f]-[1,4]diazepine.

* * * * *